United States Patent
Kampfe et al.

[11] Patent Number: 5,592,940
[45] Date of Patent: *Jan. 14, 1997

[54] PROCESS FOR MAKING DOSES FORMULATION OF CONTRAST MEDIA FROM CONCENTRATE

[75] Inventors: Michael Kampfe; Bernhard Better, both of Berlin, Germany

[73] Assignee: Schering Aktiengesellschaft, Germany

[*] Notice: The term of this patent shall not extend beyond the expiration date of Pat. No. 5,450,847.

[21] Appl. No.: 529,972

[22] Filed: Sep. 19, 1995

Related U.S. Application Data

[63] Continuation of Ser. No. 779,492, Oct. 24, 1991, Pat. No. 5,450,847, which is a continuation-in-part of Ser. No. 688,922, Apr. 22, 1991, abandoned.

[30] Foreign Application Priority Data

Jun. 29, 1991 [DE] Germany .................. 41 21 568.0

[51] Int. Cl.⁶ .................. A61B 5/05; A61B 8/00
[52] U.S. Cl. .................. 128/654; 128/653.4; 128/652.02; 141/83
[58] Field of Search .................. 424/9; 128/662.02, 128/653.1, 654; 141/83, 99, 234

[56] References Cited

U.S. PATENT DOCUMENTS

| | | | |
|---|---|---|---|
| 4,345,628 | 8/1982 | Campbell et al. | 141/83 |
| 4,350,186 | 9/1982 | Schalkowsky et al. | 141/83 |
| 4,466,442 | 8/1984 | Hilmann et al. | 128/653 |
| 4,492,281 | 1/1985 | Van Allen et al. | 177/213 |
| 4,628,969 | 12/1986 | Jurgens, Jr. et al. | 141/1 |
| 4,636,198 | 1/1987 | Stade | 604/154 |
| 4,648,430 | 3/1987 | Di Gianfilippo et al. | 141/1 |
| 4,681,119 | 7/1987 | Rasor et al. | 128/660 |
| 4,705,509 | 11/1987 | Stade | 604/154 |
| 4,718,463 | 1/1988 | Jurgens, Jr. et al. | 141/11 |
| 5,219,553 | 6/1993 | Kraft et al. | 424/9 |

FOREIGN PATENT DOCUMENTS

| | | |
|---|---|---|
| 0311229 | 4/1989 | European Pat. Off. . |
| 0650739 | 5/1995 | European Pat. Off. . |
| 0650738 | 5/1995 | European Pat. Off. . |
| 3315031 | 1/1985 | Germany . |
| 84/00139 | 1/1984 | WIPO . |
| 86/02625 | 5/1986 | WIPO . |
| 87/07237 | 12/1987 | WIPO . |

*Primary Examiner*—Francis Jaworski
*Attorney, Agent, or Firm*—Millen, White, Zelano, & Branigan, P.C.

[57] ABSTRACT

The invention relates to a process for preparing pharmaceutically acceptable dosage forms of contrast medium from concentrated contrast medium using a fluid delivery system suitable for removing predetermined amounts of fluids from a plurality of vessels and mixing same together.

38 Claims, 1 Drawing Sheet

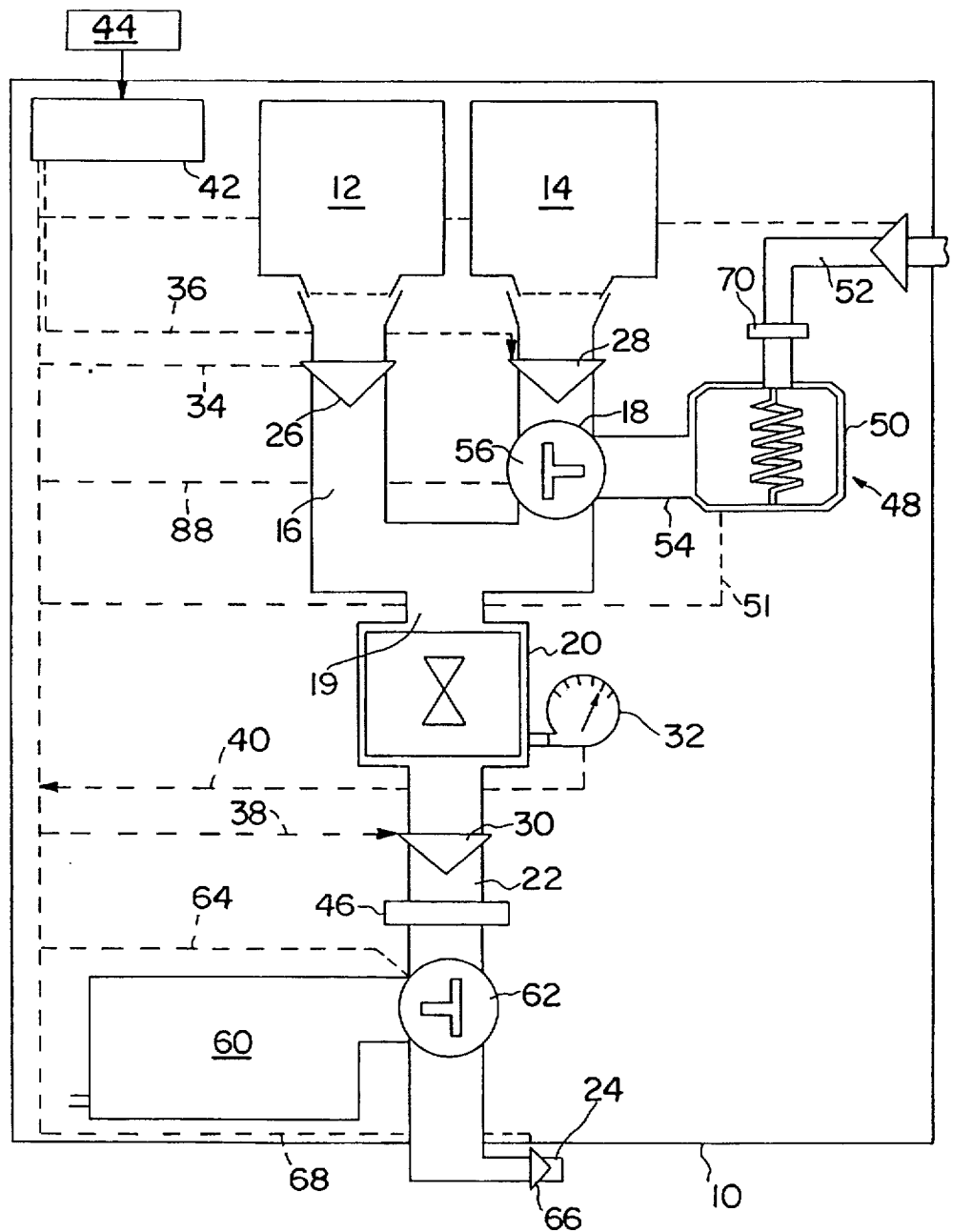

PROCESS FOR MAKING DOSES FORMULATION OF CONTRAST MEDIA FROM CONCENTRATE

CROSS-REFERENCE TO RELATED APPLICATION

This is a continuation of application Ser. No. 07/779,492,, filed Oct. 24, 1991, now U.S. Pat. No. 5450,847 which is a continuation-in-part of U.S. appln. Ser. No. 07/688,922, filed Apr. 22, 1991 and now abandoned, the entire disclosure of which is hereby incorporated by reference.

SUMMARY OF THE INVENTION

The invention relates to processes for the production of contrast medium in suitable dosage forms. Furthermore, the invention relates to methods of administrating contrast agents to a subject and a kit for use in a process of making suitable dosage forms of contrast medium.

Contrast media have become important auxiliary agents for medical diagnostic procedures such as ultrasonic, X-ray and nuclear magnetic resonance (NMR) diagnoses. For example, by administering an X-ray contrast agent to a patient, e.g., human, undergoing an X-ray examination, the contrast of the resultant image obtained is enhanced. As a result, medical personnel can better interpret the information obtained from the resultant image.

With respect to dosages, many factors must be taken into account in determining the dosage amount and dosage concentration of contrast medium which is to be administered, for example, the type of diagnostic examination involved, the manner in which the diagnostic examination is performed, the region of the patient's body which is to be examined, as well as the age, body weight and health of the patient. In view of these numerous factors, contrast media, such as X-ray contrast agents, are available in a variety of concentrations, e.g., 120 mg iodine/ml to 400 mg iodine/ml, and also a variety of dosage amounts, e.g., 1 ml–250 ml. However, despite these various concentrations and dosages amounts, not every possible situation of the individual patient is taken into account.

Despite the large number of dosage forms already commercially available (concentrations and sizes), in clinical application it is still often inevitable that only a partial amount of the selected contrast medium is used for an examination with the remainder being discarded. This results in considerable amounts of contrast medium being wasted, since use of the remaining contrast medium is contraindicated.

Because of the high number of such diagnostic examinations being performed and the expensive prices of modern contrast media, such a waste represents a considerable cost factor for a medical clinic or medical practice. Also, the need to keep numerous forms of contrast medium preparations in stock further contributes to high costs. In cases in which a new examination technique requires new preparation forms, the often long time periods involved for development and approval of new bottle sizes and/or concentrations also represent a disadvantage.

Similarly, the need of a large number of preparation forms represents disadvantages for producers of contrast media, e.g., only relatively small production batches can be produced, the storage need is increased, difficulties arise in logistics, and more expensive and prolonged development and approval times of preparations result. In addition, the flexibility of contrast media production to react to changes in preparation forms dictated by the market is slight.

These disadvantages have so far not been eliminated.

A large number of filling devices in the pharmaceutical field are known with which solutions can be mixed by portions. See, for example, from WO 84/00139 or DE-OS 33 15 031.

WO 84/00139 describes a mixing device, which exhibits suitable means for monitoring the bottling of pharmaceutical solutions. In this case, solutions are bottled, which are removed from different containers. However, specific mixing to assure homogeneous concentrations in the prepared solution suitable for use does not occur.

Also, only infusion solutions for parenteral nutrition are mixed with the mixing device known from DE-OS 33 15 031, without reference being made to the production problems of contrast medium solutions.

Moreover, both of these known devices are not suitable for mixing liquids with greatly different densities.

See also WO 86/02625, WO 87/07237 and U.S. Pat No. 4,648,430.

Therefore, an object of the invention is to make available a process of the initially mentioned type, with which patient-specific, indication-specific contrast medium compositions suitable in dosage can be produced, without a great number of forms of preparation having to be kept on hand and/or considerable amounts of waste occurring.

Moreover, contrast media and optionally desired "additives" can be administered to a patient in one application, by which the patient's comfort is increased.

Upon further study of the specification and appended claims, further objects and advantages of this invention will become apparent to those skilled in the art.

These objects are achieved by a method of preparing dosage forms of contrast medium comprising:

delivering, under sterile conditions, a predetermined amount of at least a first contrast medium concentrate in an amount of 350–450 mg of I/ml in the case of X-ray contrast media or 0.5–4 mol of contrast medium compound/liter in the case of nuclear magnetic resonance contrast media from at least a first container by a first pipe to a mixing chamber;

delivering a predetermined amount of diluent such as water or an aqueous solution from a second container by a second pipe to the mixing chamber, wherein the predetermined amounts are mixed to form a physiologically compatible preparation; and delivering the resultant mixture to a discharge station.

According to another embodiment, the inventive method comprises:

(a) providing a first vessel containing a concentrated flowable contrast medium;

(b) providing a second vessel containing a pharmaceutically acceptable diluent fluid;

(c) removing a predetermined amount of the concentrated fluid contrast medium from the first vessel via a first conduit means;

(d) removing a predetermined amount of the pharmaceutically acceptable diluent via a second conduit means; and (e) delivering the predetermined amount of concentrated contrast medium and the predetermined amount of diluent to a mixing chamber and thereby form a contrast medium in a pharmaceutically acceptable dosage form.

Dosage form is intended to mean a form of the contrast medium which has a suitable concentration for administration to a patient.

The process of the invention can be used to formulate dosage forms of any suitable contrast medium or contrast agent used in diagnostic examinations (e.g., X-ray, MRI or ultrasound).

The disadvantages discussed above concerning contrast media, delivered ready to use by the producer, can be avoided or ameliorated by preparing the dosage units on site through the use of a device which provides means for mixing together predetermined amounts of different fluids. By providing such a device, e.g., in the radiology department or hospital pharmacy, personnel can prepare suitable dosage forms or even on the day of the diagnostic examination immediately prior to a examination. By this procedure, it will be possible to produce automatically and in a sterile manner, fluid contrast medium at a concentration and in an amount which are optimal for the individual examination. Also, the contrast medium can be prepared in a way which is suitable for further use.

In the process according to the invention one or more contrast medium concentrates, in appropriate containers, which are free-flowing and highly concentrated are used. These concentrates are used in the form of solutions, dispersions or as free-flowing powder and are put into appropriate concentrate containers.

Further, one or more diluents are used for mixing with the concentrates, for example, sterile or unsterile water. Pharmaceutical solutions can also be used as diluents and/or solvents or dispersants for diluting the concentrate. Even diluted contrast medium solutions can be used for mixing with the contrast medium concentrates.

The contrast medium concentrates can exhibit concentrations which are above those which, because of application reasons (e.g., viscosity), have been produced so far. Thus, for example, X-ray contrast medium concentrates with a content of 530–450 mg of I/ml can be used or NMR contrast media (solution or dispersion) with 0.5 mol/liter (or higher) of gadopentetate dimeglumine or other NMR contrast media based on paramagnetic ions can be employed. But, of course, different contrast medium concentrates and/or different concentrations can be used for the various medical diagnostic techniques, for example, X-ray, nuclear magnetic resonance or ultrasound diagnosis.

X-ray contrast media can contain, e.g., iotrolan, iopromide, iohexol, iosimide, metrizamide, salts of amidoacetic acid, iotroxic acid, iopamidol, 5-hydroxy-acetamido-2,4,6-triiodoisophthalic acid-(2,3-dihydroxy-N-methylpropyl)-(2-hydroxyethyl)-diamide, 3-carbamoyl-5-[N-(2-hydroxyethyl)-acetamido]-2,4,6-triiodobenzoic acid[(1RS,2SR)-2, 3-dihydroxy-1-hydroxymethylpropyl]-amide and dispersions of slightly soluble X-ray contrast agents (e.g., iodipamide ethyl ester).

NMR contrast media include, e.g., gadolinium DTPA, gadolinium DOTA, gadolinium complex of 10[1-hydroxymethyl-2,3-dihydroxypropyl]-1,4,7-tris-[(carboxymethyl)-1, 4,7,10-tetraazacyclodecane], iron or manganese porphyrin chelates, and stable magnetite dispersions.

Ultrasound contrast media include, e.g., dispersions of galactose microparticles, with or without additives, in water or a galactose solution and dispersions of microspheres of entrapped air (e.g., cyano acrylates or albumin microspheres), as well as other injectable microparticles.

In accordance with the process, a predetermined amount of concentrated contrast medium is mixed with a predetermined amount of diluent, and optionally other additives, to formulate the desired dosage form of contrast medium.

Also contrast media can be mixed with one another for different fields of use. As a result with only one application two or more different examinations can be performed on the patient, which represents a marked improvement of the patient's comfort. Such a mixture of two or more contrast media is usually consumed immediately after mixing so that no stability problems arise.

The diluent is, for example, a physiologically acceptable liquid carrier medium optionally containing suitable additives. The concentrated contrast medium itself may also optionally contain suitable additives.

The diluent can be, for example, a sterile or unsterile water optionally containing buffer substances and/or isotonizing additives as well as optionally containing a complexing agent such as, e.g., $CaNa_2EDTA$.

A comparatively low concentrated contrast medium can also be used as diluent, for example, a contrast media with a concentration of 0–0.5 mol/l or 0–350 mg of I/l or 0–100 mg of particles/ml.

Suitable additives are, for example, inorganic or organic salts or buffer substances, such as sodium chloride, Tris buffer, phosphate buffer, citrate buffer, glycine buffer, citrate-phosphate buffer, maleate buffer, etc. Further included are mono- or disaccharides, such as glucose, lactose, saccharose or trehalose, sugar alcohols, such as mannitol, sorbitol, xylitol or glycerol, or water-soluble polymers, such as dextrans or polyethylene glycols.

The process can further be used to prepare dosage forms suitable for a variety of administration techniques, e.g., intravascular, subarachnoidal, intraneural, and oral administration.

Further, the process according to the invention makes possible, depending on the diagnostic formulation involved, a concentration or volume change of the contrast medium during application. Thus, different concentrations or volumes can be automatically produced and applied successively in situ.

Also, it is possible to change the originally provided dosage form, relative to the concentration or volume, during the examination if the originally applied dose does not produce the desired diagnostic result.

As mentioned above, the concentrated contrast agent is in a free-flowing form such as a solution, dispersion or powder. In the latter case, the diluent can act as a solvent and/or dispersion medium.

A device for performing the process according to the invention comprises at least one contrast medium concentrate container and at least one diluent container. A predetermined amount of fluid is removed from each of these containers. Removal can be performed simultaneously or successively. The removed predetermined amounts of fluid are fed to a mixing zone or a mixing chamber, in which the two fluids are mixed, and a homogeneous contrast medium is obtained in a suitable dosage form. The concentrate container and the diluent container are each connected by pipes or conduits to the mixing zone. Conveying of the fluids can take place either automatically by the effect of gravity or by active pump influence, for example, a vacuum pump or a peristaltic pump.

If conveying takes place by effect of gravity, shutoff devices, for example valves, are provided in each of the feed pipes connecting the concentrate container(s) diluent container(s) to mixing zone. The shutoff devices are, for example, activated in a predetermined way by a control unit. Thus, the amount of fluid present in the respective container, the pipe cross section as well as the pipe length determine the feed rate and the amount of fluid flowing into the mixing zone.

If, on the other hand, a peristaltic pump is used, the pump in the inactivated state acts as shutoff unit. But, in the activated state, it pumps fluid from the respective container into the mixing zone. If the fluid is pumped with a vacuum pump, shutoff elements are employed in the feed pipes and are activated together with the vacuum unit.

The individual feed pipes can be connected directly to the mixing chamber. Alternatively, a feed pipe from a concentrate container and a feed pipe from a diluent container can be joined before the mixing chamber with a single pipe leaving the junction point to connect with the mixing chamber so that a Y connection is formed.

To insure accurate determination of the amount and concentration of the dosage form, the device is preferably provided with units for determining the amount of fluids removed from the respective containers. Such units include, for example, flow sensors in the feed pipes, with which the amount of fluid flowing per unit of time can be determined. On the other hand, scales can also be used, which determine either the increase of the amounts of fluid in the mixing chamber or else the respective decrease of the amounts of fluid in the respective container(s). Volumetrically operating units can also be placed on the mixing chamber or the output container, with which the inflowing volume or the outflowing volumes can be determined.

In any case, the outflowing or inflowing amounts of fluid or fluid volumes can be determined exactly with these sensors as a function of the activation time of the shutoff elements or pumps. These sensors are electrically linked to the control unit and send appropriate signals to the control unit as respective set point.

The control unit itself calculates from the transmitted signals the respective amounts, volumes and/or concentrations of the conveyed masses or of the mixture present at the moment in the mixing chamber. As is known, desired concentrations of the preparation form can be reliably controlled by the specific density or densities of the contrast medium compound(s) used.

Iodinated X-ray contrast media typically have a high density. For example, ULTRAVIST 370® has a density of 1.41 g/cm$^3$ and ANGIOGRAPIN® 65% has a density of 1.35 g/cm$^3$. For this reason, density provides a reliable indicator for determination of concentration. In such a case, a density sensing means can be provided within the mixing chamber can also be employed. On the other hand, the optical rotation can also be a suitable determination parameter. Of course, volumetric or gravimetric determination parameters, among others can also be used.

As stated above, the actual signal for control unit is used for controlling the pumps or the shutoff elements as a function of a previously established setpoint, which can be input manually in the control unit by an input unit.

The control unit sends appropriate control signals for activation of the shutoff elements and pumps and receives the sensor signals, which relate to the amounts of fluid removed from the containers and/or delivered to the mixing chamber.

In addition, the device can be further provided with temperature control means for controlling temperature of fluids within the containers, pipes, mixing chamber or at the fluid outlet of the device. Temperature control can facilitate control of the density of the fluids and also aid in providing a contrast media having a temperature which is comfortable to the patient.

The mixing chamber is connected to a receiving means for receiving the resultant homogeneously mixed contrast media. For example, the mixing chamber can be connected by a delivery pipe to a means for administering the contrast agent, e.g., hypodermic syringes, which are successively filled with the contrast agent in the desired dosage form. The mixing chamber can also alternatively be connected to container(s) for storage, cartridge(s) for pressure injectors, or directly to a patient for direct infusion.

The mixing chamber device can be connected to empty sterile containers (e.g., sealed by a septum) to be used for holding the contrast agent in its dosage form. In this case, sterile infusion or injection vials made of plastic or glass or infusion bags can be used.

According to another embodiment, the device can be connected directly to an extruder for making suitable plastic containers. The device can be used to directly fill such empty containers or an injection syringe or can provide direct infusion to a patient.

According to another advantageous embodiment, the feed pipe arrangement is connected to an additional vessel(s) containing a cleaning and/or rinsing liquid. In this way, the conduits, shut-off valves, pumps, mixing chamber, collection chamber, containers, etc., can be flushed with cleaning fluid. The liquid can be any suitable cleaning medium, e.g., sterile or unsterile water with or without additives. In addition, the diluent itself could be used as a rinsing fluid.

The device can be further provided with a collection chamber wherein fluid employed during cleaning stages of operation is collected. Rinsing can be preformed preferably after each dosage formulation.

In a further advantageous embodiment, the device is connected to a sterilization unit. The sterilization unit can, for example, comprise a steam generator and a means to deliver sterilizing steam into the conduits, valves, pumps, containment vessels, etc.

On the other hand, a liquid disinfectant, for example, peracetic acid, can also be used as the sterilization medium. In such a case, after the sterilization process, care must be taken that possible disinfectant residues are removed with sterile water. Sterilization of the device is preferably performed less frequently than rinsing.

Advantageously, the sterilized device is kept in sterilized condition with sterile filters inserted in the pipe sections.

The containment vessel for the concentrated contrast medium can be of any suitable size, e.g., 1–100 liters, especially 1 liter, 5 liters, 10 liters, 50 liters, etc. The containers can be made out of any material suitable for storage of concentrated pharmaceutically acceptable contrast medium and preferably suitable for sterilization, e.g., heat-resistant plastic, glass or metal. These containers can either be reused or else are suitable only for a single use.

Furthermore, the mixing effect in the mixing zone or mixing chamber can be improved by providing a stirring device in the mixing zone or mixing chamber.

The device according to the invention has several advantages. For example, an automated contrast media delivery system as described above with its subsequent sterilization and sterile maintenance features will present a smaller risk of contamination. In addition, by using the delivery system according to the invention, it is possible to add admixtures such as electrolytes and pharmaceutical-compositions as heparin, prostacyclins, corticoids, etc.

The automated contrast media delivery system according to the invention also permits the injection of contrast media in a pattern. This ability could be useful in, for example, "one film" urography. In such studies, it is normally required to take several images at different time periods, e.g., 5, 10, 20 minutes, to obtain an overview of the entire urinary tract. By injecting different concentrated contrast media in a desired pattern, better results may be obtained.

Moreover, through use of the automatic contrast media delivery system according to the invention, it is possible to dispense media under standardized, reproducible conditions. Such an ability is especially significant in the case of ultrasound contrast media.

Preferably, the contrast medium within the containment vessel will be at a high concentration. A concentrated solution and/or dispersion means a solution at a concentration which is equal or higher than that of conventional commercial dosage forms of the contrast agent. For example, in the case of an iodinated X-ray contrast agent, the concentration of the contrast agent in the containment vessel can be about 350 mgI/ml–450 mgI/ml. With respect to NMR contrast agents, gadopentetate dimeglumine (dimeglumine Gd-DTPA) is generally commercially available at concentrations of 0.5 mol/liter. Consequently, concentrated solutions or dispersions of NMR contrast agent exhibit an equal or higher concentration than, e.g., 0.5 mol/liter, especially 0.5–4 mol/liter.

While the inventive process is preferably used for making suitable dosage forms from concentrated contrast medium, it is also possible to use the process according to the invention to decrease the concentration of commercially available dosage forms of contrast media.

In accordance with another aspect of the invention, there is provided a kit for use with a fluid delivery system as discussed above for the formulation of suitable dosage forms of contrast medium. The kit will contain a first containment vessel containing concentrated contrast media and a second containment vessel containing suitable diluent. The containment vessels of the kit preferably have means for connection to a device according to the invention for the delivery of predetermined fluid amounts from each of the vessels to a mixing chamber. For example, a kit would comprise a first containment vessel containing 0.1–100 liters, e.g., 1–100 liters, of concentrated X-ray contrast agent at a concentration of 530–450 mgI/ml and a second containment vessel containing 1–100 liters of diluent suitable for the formulation of X-ray contrast medium in pharmaceutically acceptable forms. Alternatively, the kit could comprise a first containment vessel containing 100 ml to 100 l of NMR contrast agent at a concentration of 0.5–4 mol/l.

BRIEF DESCRIPTION OF THE DRAWINGS

Various other objects, features and attendant advantages of the present invention will be more fully appreciated as the same becomes better understood when considered in conjunction with the accompanying drawing, in which like reference characters designate the same or similar parts throughout the several views, and wherein:

FIG. 1 illustrates a fluid dispensing device according to the invention.

DETAILED DESCRIPTION OF THE DRAWING

Device 10 shown in FIG. 1 exhibits a container 12 for a contrast medium concentrate and a container 14 for a solvent or diluent. The two containers 12 and 14 are connected to a mixing chamber 20 by feed pipes 16 and 18. In the illustrated embodiment, the two pipes 16 and 18, upstream from mixing chamber 20, are brought together to form a single pipe 19 which then empties into mixing chamber 20. Such a connection is not, however, necessary. Consequently, the two pipes 16 and 18 can also be individually connected directly to mixing chamber 20.

A delivery pipe 22, for fluid discharge is also connected to mixing chamber 20. End 24 of pipe 22 can be connected with a variety of receiving containers (not shown), e.g., vials, bags or syringe arrangements.

A first metering element 26 is inserted in first feed pipe 16 and a second metering element 28 is inserted in second feed pipe 18. Moreover, a third metering element 20 is inserted in delivery pipe 22.

Mixing chamber 20 is connected to a weighing device 32, which can detect the respective weight condition of mixing chamber 20.

Metering elements 26, 28 and 30, as well as weighing device 32 are connected by signal lines 34, 36, 38 and 40, to a control unit 42. Control unit 42 exhibits an input unit 44, with which specific data can be input into control unit 42.

According to a preferred embodiment, a sterile filter 46 is provided in delivery pipe 22 downstream from the third metering element 30.

Advantageously, device 10 is also provided with a sterilization unit 48, which, for example, exhibits a steam generator 50 connected by a feed pipe 52 to a water source (not shown). Steam generator 50 is connected by a delivery pipe 54 to feed pipes 16 and 18. At the connection point a shutoff device 56 in the form of a three-way valve is provided. This shutoff device 56 can also be connected by a signal line 58 to control unit 42.

Downstream from mixing chamber 20, a storage chamber 60, is provided for receiving flushing solutions and the like from delivery pipe 22. Storage chamber 60 is connected to delivery pipe 22 by a shutoff device 62 in the form of a three-way valve. The activation of shutoff device 62 takes place by a signal line 64 connected to control unit 42.

Further a discharge valve 66, also connected by a signal line 68 to control unit 42, is provided at the end of delivery pipe 22. Finally, steam generator 50 is connected by a signal line 51 to control unit 42.

Device 10, as shown in FIG. 1, contains the abovementioned concentrates and diluents in the two containers 12 and 14. Device 10 is not, however, limited to only two containers 12 and 14, but can exhibit a great number of these containers, which in each case are in fluid communication with the mixing chamber via feed pipes. The feed pipe are provided with corresponding shutoff or metering elements.

Metering elements 26, 28 and 30 in feed pipes 16 and 18 and delivery pipe 22 operate under the force of gravity. That is, in the activated condition metering elements 26, 28 and 30 are open and, in this open mode permit the respective fluids to pass through. In this respect they act as shutoff devices. They can also be replaced by other metering devices, for example, peristaltic pumps, which in the inactivated condition act as shutoff elements and in the activated condition convey the respective upstream fluid.

The device shown in FIG. 1 is operated as follows:

The contrast medium present in container 12 exhibits—as initially described—a specific composition and concentration. Both the contrast medium used and its concentrate concentration can be input into control unit 42 by input unit 44. To produce a finished usable contrast medium in mixing chamber 20, the operator inputs via input unit 44 the amount of contrast medium to be mixed, after which the control unit 42 calculates from the respective amounts of preset contrast medium concentrate and diluent to be conveyed to mixing chamber 20 from containers 12 and 14. Metering elements 26 and 28 are successively opened, and the respective fluids flow from containers 12 or 14 into mixing chamber 20.

The content of mixing chamber 20 is monitored by, for example, scale 32. After reaching the desired amount of first material (for example, the concentrate amount) as determined by control unit 40, metering element 26 is deactivated and metering element 28 is activated. After reaching the desired amount of second material (e.g., diluent) in mixing chamber 20, metering element 28 is deactivated. Then the third metering element 30 and optionally discharge valve 66 are activated to convey either a part or the entire amount of contrast medium contained in mixing chamber 20, to discharge outlet 24 of delivery pipe 22. Thus, consequently, third metering element 30 can be used not only in the production of a preparation but also of several preparations from mixing chamber 20.

It is also possible to employ a volume measuring unit in place of weighing unit 32 for the determination of the amounts of fluid flowing into mixing chamber 20.

Since a sterile filter 46 is provided downstream from metering element 30, all units, which are upstream from this sterile filter 46, remain in the sterilized condition.

After emptying of mixing chamber 20 or containers 12 and 14, the entire device 10 is sterilized by sterilizing unit 48. Sterilizing stream is conducted through the entire pipe arrangement 16, 18, 22, mixing chamber 20 and sterile filter 46 to storage chamber 60.

Finally, a pyrogen filter 70 can also be provided in fresh water feed pipe 52 to effectively retain pyrogens possibly present in the inflowing water. This sterile water can be used, just as the diluent in container 14, for flushing purposes in a separate flushing operation.

The entire disclosures of all applications, patents and publications, cited above and below, and Federal Republic of Germany P 41 21 568.0, filed Jun. 29, 1991, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a diagnostic contrast medium comprising at least one contrast agent and an aqueous solution, said process comprising:
    delivering, under sterile conditions, a predetermined amount of at least a first contrast medium concentrate containing 340–450 mg of I/ml of X-ray contrast agent, 0.5–4 mol of NMR contrast agent/liter, or an ultrasound contrast agent, from at least a first container by a first pipe to a mixing chamber;
    delivering a predetermined amount of diluent from a second container by a second pipe to the mixing chamber, wherein said predetermined amounts are mixed to form a physiologically compatible preparation; and
    delivering the resultant mixture to a discharge station.

2. A process according to claim 1, wherein said concentrate is in liquid, form.

3. A process according to claim 1, wherein said contrast agent is iotrolan, iopromide, iohexol, iosimide, metrizamide, a salt of amidoacetic acid, iotroxinic acid, iopamidol, 5-hydroxyacetamido-2,4,6-triiodo-isopththalic; acid-(2,3-dihydroxy-N-methylropyl)-(2-hydroxyethyl)-diamide, 3-carbamoyl-5-[N-(2-hydroxyethyl)-acetamido]-2,4,6-triiodobenzoic acid-[(1RS, 2SR)- 2,3-dihydroxy-1-hydroxymethylpropyl]-amide, dispersions of iodipamide ethyl ester, gadolinium DTPA, gadolinium DOTA, gadolinium complex of 10[1-hydroxymethyl-2,3-dihydroxy-propyl]-1,4,7-tris[(carboxymethyl)-1,4,7,10-tetraaza-cyclodecane], an iron porphyrin chelate, a manganese porphyrin chelate, a stable magnetite dispersion, an aqueous dispersion of galactose microparticles, a galactose solution, or a dispersion of microspheres containing trapped air.

4. A process according to claim 3, wherein said contrast agent is a dispersion of cyanoacrylate and/or albumin microspheres of trapped air.

5. A process according to claim 1, wherein said diluent is water or an aqueous solution.

6. A process according to claim 1, wherein said diluent is an aqueous medium containing:
    0–0.5 mol/l of NMR contrast agent, 0–350 mg of I/ml of X-ray contrast agent and/or
    medicinally active substances, and/or
    buffer substances, and/or
    isotonically active additives, and/or
    complexing agents.

7. A process according to claim 1, wherein said concentrate is in powdered form.

8. A process according to claim 1, wherein said first contrast medium concentrate and said diluent are conveyed to said mixing chamber by gravity.

9. A process according to claim 1, wherein said first contrast medium concentrate and said diluent are conveyed to said mixing chamber by pump.

10. A process according to claim 1, wherein said first pipe and said second pipe are joined together upstream of the mixing chamber at a junction point and a single pipe connects said junction point to said mixing chamber.

11. A device for production of a contrast medium, comprising:
    at least one concentrate container containing concentrated contrast media;
    at least one diluent container containing a diluent suitable for use with contrast media;
    a first feed pipe and a second feed pipe in connection with, respectively, said concentrate container and said diluent container, said feed pipes also being in fluid communication with a mixing chamber;
    a delivery pipe in fluid communication with said feed pipes;
    a mixing chamber provided between said feed pipes and said delivery pipe;
    metering elements in said feed pipes which meter, respectively, predetermined amounts of said concentrated contrast media and said diluent;
    means for determination of metered amounts of said concentrated contrast media and said diluent;
    metering device in said delivery pipe, which discharges contrast medium from an end of said delivery pipe;
    and a control unit which controls said metering elements.

12. A device according to claim 11, wherein the end of said delivery pipe is connected to a container or a syringe for receiving the resultant contrast medium.

13. A device according to claim 11, wherein said device further comprises shut-off elements in said first feed pipe, said second feed pipe and said delivery pipe, and wherein said control unit also controls said shut-off elements.

14. A device according to claim 13, wherein said means for determination is a weighing device connected to said mixing chamber and to said control unit.

15. A device according to claim 11, wherein said first feed pipe and said second feed pipe are provided with flow sensors.

16. A device according to claim 11, further comprising a density sensing means within said mixing chamber.

17. A device according to claim 11, further comprising at least one temperature control means for controlling fluid temperature.

18. A kit for production of a contrast medium, comprising:
 a concentrate containing 530–450 mg of I/ml of X-ray contrast agent, 0.5–4 mol/liter of NMR contrast agent or a concentrated ultrasound contrast agent in a first container with a volume of 0.1–100 l; and
 an aqueous diluent in a second container with a content of 1–100 liters.

19. A kit according to claim 8, wherein the agent of said concentrate contains as compound iotrolan, iopromide, iohexol, iosimide, metrizamide, a salt of amidoacetic acid, iotroxinic acid, iopamidol, 5-hydroxy-acetamido-2,4,6-tri-iodo-isophthalic acid-(2,3-dihydroxy-N-methylpropyl)-(2-hydroxyethyl)-diamide, 3-carbamoyl-5[N-(2-hydroxy-ethyl)-acetamido]-2,4,6-triiodobenzoic acid[(1RS,2SR)-2,3-dihydroxy-1-hydroxymethylpropyl]-amide, dispersions of iodipamide ethyl gadolinium DTPA, gadolinium DOTA, gadolinium complex of 10[1-hydroxymethyl-2,3-dihydroxypropyl]-1,4,7-tris[(carboxymethyl)-1,4,7,10-tetraazacyclodecane], an iron porphyrin chelate, a manganese porphyrin chelate, a stable magnetite dispersion, an aqueous dispersion of galactose microparticles, a galactose solution, or a dispersion of microspheres containing trapped air.

20. A kit according to claim 18, wherein said first container contains 1–100 liters of concentrated X-ray contrast agent at a concentration of 350–450 mgI/ml and said second container contains 1–100 liters of said diluent.

21. A kit according to claim 18, wherein said NMR contrast agent is gadolinium DTPA, gadolinium DOTA, gadolinium complex of 10[1-hydroxymethyl-2,3-dihydroxypropyl]1,4,7-tris[(carboxymethyl)-1,4,7,10-tetraazacyclododecane], or an iron porphyrin chelate, a manganese porphyrin chelate, or a stable magnetite dispersion.

22. A kit according to claim 18, wherein said ultrasound contrast agent is an aqueous dispersion of galactose microparticles, a galactose solution, or a dispersion of microspheres containing trapped air.

23. A method of preparing a diagnostic contrast medium in dosage form, comprising:
 (a) providing a first vessel containing a concentrated flowable contrast medium;
 (b) providing a second vessel containing a pharmaceutically acceptable diluent fluid;
 (c) removing a predetermined amount of said concentrated fluid contrast medium from said first vessel via a first conduit means;
 (d) removing a predetermined amount of said pharmaceutically acceptable diluent via a second conduit means;
 (e) delivering said amount of contrast medium and said amount of diluent to a mixing chamber and
 (f) forming a contrast medium in a pharmaceutically acceptable dosage form within said mixing chamber.

24. A method according to claim 23, wherein said predetermined amount of concentrated fluid contrast medium and said predetermined amount of pharmaceutically acceptable diluent are simultaneously removed from said first vessel and said second vessel, respectively.

25. A method according to claim 23, wherein said predetermined amount of concentrated fluid contrast medium and said predetermined amount of pharmaceutically acceptable diluent are successively removed from said first vessel and said second vessel, respectively.

26. A method according to claim 23, wherein said concentrated fluid contrast medium and said pharmaceutically acceptable diluent are mixed within said mixing chamber to form a homogeneous contrast medium.

27. A method of preparing diagnostic contrast medium in dosage form, comprising:
 (a) connecting a first vessel and a second vessel to a device for combining predetermined amounts of fluids from separate vessels, said first vessel containing concentrated flowable contrast medium and said second vessel containing a pharmaceutically acceptable diluent fluid;
 (b) removing a predetermined amount of said concentrated contrast medium from said first vessel via a first conduit means;
 (c) removing a predetermined amount of said pharmaceutically acceptable diluent via a second conduit means;
 (d) delivering said amount of contrast medium and said amount of diluent to a mixing chamber; and
 (e) forming a contrast medium in a pharmaceutically acceptable dosage form.

28. A method of preparing a diagnostic contrast medium in dosage form, comprising:
 (a) providing a device for combining predetermined amounts of fluids from separate vessels, said device comprising:
  (i) means for connecting a first vessel;
  (ii) means for connecting a second vessel;
  (iii) a first conduit means for removing flowable material from said first vessel;
  (iv) a second conduit means for removing flowable material from said second vessel;
  (v) a first fluid flow regulation means for controlling fluid flow in said first conduit means;
  (vi) a second fluid flow regulation means for controlling fluid flow in said second conduit means;
  (vii) a mixing chamber, in fluid communication with said first conduit means and second conduit means, for receiving amounts of flowable material from said first vessel and said second vessel, which is provided with means for mixing fluid from said first vessel and fluid from said second vessel to form a homogeneous mixture;
  (viii) sensing means for sensing the amount of flowable material removed from said first vessel in said second vessel, the amount of flowable material delivered to said mixing chamber and/or the concentration of material in said mixing chamber;
  (ix) control means, in connection with said sensing means and said fluid flow regulation means in said first and second conduit means, for regulating flow into said mixing chamber and determining the amounts of material removed from said first and second vessels and/or delivered to said mixing chamber and/or the concentration in said mixing chamber;
 (b) connecting a first vessel containing concentrated flowable medium to said contact means for connecting a first vessel;
 (c) connecting a second vessel containing a pharmaceutically acceptable fluid diluent to said means for connecting a second vessel;
 (d) removing contrast medium and fluid diluent from said first and second vessels via said first and second conduit means and delivering said fluid contrast agent in fluid diluent to said mixing chamber,
whereby the resultant combination of said fluid contrast medium and said fluid diluent forms a pharmaceutically acceptable dosage form of said contrast medium.

29. A method according to claim 28, further comprising:

detecting the concentration of contrast medium contained in said mixing chamber by sensing the density of the resultant mixture in said mixing chamber.

30. In a method of preparing a dosage form of diagnostic contrast medium comprising combining a concentrated flowable contrast medium and a diluent, the improvement comprising:

employing a fluid delivery device suitable for removal of predetermined amounts of fluid from a plurality of vessels to remove an amount of said concentrated flowable contrast medium from a first vessel and an amount of said diluent from a second vessel; and combining and mixing said amounts of concentrated contrast medium and diluent in a mixing chamber to form homogeneous contrast medium in a pharmaceutically acceptable dosage form.

31. A method according to claim 30, wherein said diagnostic contrast medium is an iodinated X-ray contrast agent.

32. A method of administering a contrast medium in dosage form comprising:

(a) preparing a diagnostic contrast medium in dosage form according to the method of claim 23, and (b) administering a dose of said diagnostic contrast medium to a patient.

33. A method according to claim 32, further comprising:

providing means for placing said mixing chamber in fluid communication with a patient, and administering said contrast medium to said patient by direct infusion.

34. A method according to claim 32, further comprising:

placing said mixing chamber in fluid communication with a sterile sealed container.

35. A method according to claim 32, further comprising:

placing said mixing chamber in fluid communication with a cartridge for an injector.

36. A method according to claim 32, further comprising:

placing said mixing chamber in fluid communication with a hypodermic syringe.

37. In a method of X-ray diagnostic examination comprising administering an X-ray contrast agent to a patient, the improvement wherein:

said X-ray contrast agent is administered to said patient in accordance with claim 32.

38. In a method of NMR imaging comprising administering an NMR contrast agent to a patient, the improvement wherein:

said NMR contrast agent is administered to said patient according to claim 32.

* * * * *